(12) United States Patent
Sutko et al.

(10) Patent No.: US 7,960,702 B2
(45) Date of Patent: Jun. 14, 2011

(54) PHOTON EVENT DISTRIBUTION SAMPLING APPARATUS AND METHOD

(75) Inventors: John L. Sutko, Reno, NV (US); Nelson G. Publicover, Reno, NV (US)

(73) Assignee: Board of Regents of the Nevada System fo Higher Education, on behalf of the University of Nevada, Reno, Reno, NV (US)

( * ) Notice: Subject to any disclaimer, the term of this patent is extended or adjusted under 35 U.S.C. 154(b) by 1147 days.

(21) Appl. No.: 11/597,028

(22) PCT Filed: May 20, 2005

(86) PCT No.: PCT/US2005/017948
§ 371 (c)(1),
(2), (4) Date: Nov. 17, 2006

(87) PCT Pub. No.: WO2005/115005
PCT Pub. Date: Dec. 1, 2005

(65) Prior Publication Data
US 2008/0025462 A1    Jan. 31, 2008

Related U.S. Application Data

(60) Provisional application No. 60/573,459, filed on May 20, 2004.

(51) Int. Cl.
*G01J 1/00* (2006.01)
*G01B 11/00* (2006.01)
(52) U.S. Cl. .................................................. 250/395
(58) Field of Classification Search ............... 250/336.1, 250/370.08, 584, 395; 356/614, 629
See application file for complete search history.

(56) References Cited

U.S. PATENT DOCUMENTS

| | | | |
|---|---|---|---|
| 5,825,033 A | 10/1998 | Barrett et al. |
| 5,865,978 A | 2/1999 | Cohen |
| 5,953,133 A | 9/1999 | Fujimiya et al. |
| 6,271,916 B1 | 8/2001 | Marxer et al. |
| 6,606,153 B2 | 8/2003 | Marxer et al. |
| 7,009,172 B2 | 3/2006 | Publicover et al. |
| 2001/0030800 A1 | 10/2001 | Engelhardt et al. |
| 2001/0047682 A1 | 12/2001 | Samsavar et al. |
| 2003/0089162 A1 | 5/2003 | Samsavar et al. |

OTHER PUBLICATIONS

U.S. Appl. No. 11/986,371, filed Nov. 21, 2007, Sutko, et al. Porta, D., International Search Report for international application No. PCT/US05/017948, 2 pp. (Jul. 11, 2008).
Porta, D., Written Opinion of the International Searching Authority for international application No. PCT/US05/017948, 7 pp. (Jul. 11, 2008).

*Primary Examiner* — David P Porta
*Assistant Examiner* — Mark R Gaworecki
(74) *Attorney, Agent, or Firm* — Klarquist Sparkman, LLP

(57) ABSTRACT

Locations of the origins of the photons are acquired from a scanned sample with reference to a scan frame. The location on the sample from which a photon was emitted is inferred from the location of the scan as commanded by a scan drive signal, a feedback signal related to the position of the scan device, or alternatively by the point in time during a scan at which the photon is detected. A position function, e.g., photon probability density, is associated with a photon position. Summing or other processing of photon probability density functions can require fewer photons to converge to an ideal density distribution associated with an image feature than are required using conventional pixel binning. Stored data can be mapped into pixels or voxels of a display or otherwise processed. Original data remains available in the digital storage for post-hoc analysis. Imprecision introduced by the display process need not adversely affect the precision of the collected data.

40 Claims, 6 Drawing Sheets a.

Distributive    Associative b.    c.

b a b a

PHOTON EVENT DISTRIBUTION SAMPLING APPARATUS AND METHOD

CROSS REFERENCE TO RELATED APPLICATIONS

This is the U.S. National Stage of International Application No. PCT/US2005/017948, filed May 20, 2005, which was published in English under PCT Article 21(2), which in turn claims the benefit of U.S. Provisional Application No. 60/573,459, filed May 20, 2004. Both applications are incorporated herein in their entirety.

STATEMENT OF GOVERNMENT SUPPORT

The invention was made by an agency of the United States Government or under a contract with an agency of the United States Government. The name of the U.S. Government agency and the Government contract number are: National Science Foundation, Grant/Contract No. EPS0132556. The U.S. Government has certain rights in the invention.

FIELD OF INVENTION

This invention concerns high sensitivity imaging apparatus, especially optical systems for examining reflected, fluorescent or chemiluminescent radiation.

BACKGROUND OF THE INVENTION

Detecting photons and producing electronic images from a scanned field of view has been performed to produce electronic outputs representing the field of view of an instrument, such as a laser scanning confocal microscope. In this regard, the term "photon" means a unit of electromagnetic energy irrespective of its position in the spectrum, e.g. visible or invisible radiation. In quantum physics, a photon is characterized as a particle or a wave. The nature of the present invention and the manner of its use are not dependent on whether or not the photon is a particle or a wave.

In one prior art optical detection technique, photons are directed by a confocal imager in the confocal microscope to be sensed by a detector. A confocal imager comprises a point source of light that illuminates a spot within a sample. In order to illuminate an entire sample with a spot, the light source is scanned across a sample by a beam steering device using scanners that are well known in the art. An illuminated spot is then imaged onto a detector through a pinhole, or "point" aperture. Detectors comprise, for example, avalanche photodiode arrays or photomultiplier tubes.

The light source, the illuminated spot, and the detector have the same foci; they are placed in conjugate focal-planes. They are therefore "confocal" to each other.

The diameter of the detector aperture is preferably matched to the illuminated spot through the intermediate optics. Because a small spot is illuminated and then detected through a small aperture, only the plane in focus within the specimen is imaged on to the detector. The detector produces output pulses indicative of detected photons.

The detector output pulses are processed to provide information such as time-correlated photon-counting histograms and image generation in conventional laser scanning. In conventional imaging systems, however, photons obtained over each of a number of successive, selected equal time periods defined by a pixel clock are used to generate an intensity value assigned to each pixel (two-dimensional area of a portion of an image). Photon counts are binned, that is, accumulated as a group, during each sampling period corresponding to a pixel location of an image display. In this manner, a computer builds up an entire image one pixel at a time to produce an entire two-dimensional image often made up of thousands or multiple millions of pixels. In three-dimensional imaging, successive two-dimensional layers of a sample are scanned, and the computer builds up an image comprising voxels.

In producing a conventional image, a scan rate is selected. As scan rate increases, fewer photons per pixel per scan are accumulated, and intensity of pixels and signal-to-noise ratio therefore decrease. As a result, prior art pixel-based imaging systems face constraints in scan rate with regard to the quality of output signal to be produced. Physical and mechanical constraints, such as the rate at which a scanner can move, are also present. In addition, the number of photon counts in a sample affects other parameters relating to intensity. These parameters include signal-to-noise ratio.

As a result, pixel based scanning typically allows for reduced flexibility in experiment design. Resolution of the location of each photon is limited to the dimensions of a pixel or voxel as applicable. The amount of excitation illumination required for output data to reach convergence of features of sensed images is proportional to the number of photons that must be produced to provide data sufficient to reach this convergence. When pixels are of smaller dimension and therefore provide fewer photons per scan, samples often must be subjected to excitation radiation a larger number of times than if the pixels were larger.

The requirement for greater illumination has functional drawbacks. In the subset of applications using fluorescent samples, many molecules under test can fluoresce only a limited number of times. At some point, response to excitation radiation ceases, and an effect known as photo-bleaching occurs. Over illumination also presents another drawback. Where measurements are made in vivo, emission of a photon from tissue causes free radicals, which can damage cells. Therefore, over-illumination of tissue can result in photo-toxicity.

A limitation of typical prior art techniques is that they are optically based. Optically based techniques have an inherent limit of resolution known as a diffraction limit, which may be ~0.6λ, where λ is the wavelength of the illuminating light. The resolving power of a lens is ultimately limited by diffraction effects. The lens' aperture is a "hole" that is analogous to a two-dimensional version of the single-slit experiment. Light passing through it interferes with itself, creating a ring-shaped diffraction pattern known as the Airy pattern, that blurs the image. An empirical diffraction limit is given by the Rayleigh criterion:

$$\sin\theta = 1.22\frac{\lambda}{D}$$

where θ is the angular resolution, λ is the wavelength of light, and D is the diameter of the lens. A wave does not have to pass through an aperture to diffract. For example, a beam of light of a finite size passing through a lens also undergoes diffraction and spreads in diameter. This effect limits the minimum size d of spot of light formed at the focus of a lens, known as the diffraction limit:

$$d = 2.44\lambda \frac{f}{a},$$

where λ is the wavelength of the light, f is the focal length of the lens, and a is the diameter of the beam of light, or (if the beam is filling the lens) the diameter of the lens. Optical techniques do not afford the opportunity to obtain resolution beyond the diffraction limit.

SUMMARY

The Applicants have discovered that prior art pixel-based imaging techniques lose information. For example, information typically is lost due to binning of photons.

The Applicants have also discovered that, in pixel or voxel based sampling systems, more photons typically are detected than would be necessary if the system did not lose data due to use of the pixel sampling paradigm. In the pixel sampling paradigm, photons collected during a predefined pixel clock interval are summed. This summing results in the loss of spatial and temporal information for individual photons.

Briefly stated, in accordance with certain embodiments of the present invention, an apparatus and a method are provided for use with a scanned sample emitting photons during a scan period in which the location, or site, of the origin of individual protons, or sets of photons, can be determined and recorded. The locations of the sources of individual photons or sources of photons are acquired in a "pixel-less" manner to yield position information from a detected photon. The locations of the origins of the photons are acquired with reference to a scan frame that may be defined as a single instance of a scan pattern.

In one embodiment, the scanner traverses the scan pattern over one scan period. During each successive scan, the scanner may have the same location at the same elapsed time from the beginning of the scan period. Therefore, during a scan, a current x-y location of the scanner may have a one-to-one correspondence with a value of a signal associated with scan position. One such signal may be a value of input to a scan driver. Another such signal may be elapsed time from the beginning of a scan. By measuring elapsed time in relation to the beginning of a scan period, position of the scanner may thus be determined. Another such signal may be values of position feedback from the scan device.

Elapsed time may also be measured from a time the scanner has a known location rather than the beginning of a scan. The time of occurrence of detection of each photon is registered. The location on the sample from which a photon was emitted is inferred from the location of the scanner at the time at which the photon is detected.

Certain embodiments measure each photon position by a position function associated with the position. One exemplary position function is photon probability density. The technique then sums or otherwise processes the photon probability density functions, which can require fewer photons to converge to an ideal density distribution associated with an image feature than are required using conventional pixel binning. Consequently, the same number of photons may be counted to yield increased spatial resolution. Sensitivity of measurement can be improved. Since fewer photons need be detected for a given resolution, less excitation illumination of a sample to produce photons is required than with conventional pixel binning. The technique thus can eliminate or reduce over-illumination of samples and its concomitant adverse effects.

In certain embodiments, image frames may be constructed by summing the spatial distribution of photons over any user-selected time period rather than the specific period of a pre-selected pixel or voxel. Images can be displayed in raster space after they are stored digitally. Consequently, any imprecision introduced by the display process need not adversely affect the precision of the collected data. The original precise location data remain available in the digital storage.

Since some embodiments can provide high resolution in scan location, these embodiments also can provide high resolution in photon location. In one embodiment, photon location corresponds to an analog signal that is converted to a digital signal having a preselected number of bits. This number of bits can be selected so that the generated image can be based in effect on photon location data having a number of bits corresponding to a resolution of several megapixels per image or more in display space. Quality of a displayed image is limited only by the quality of display apparatus and not by the quality of the data.

Other techniques may be utilized to implement differing embodiments of the invention. In one form, intervals between detections of individual photons are recorded. Various points in time displaced by equal intervals may each correspond to a milepost location of a scan. A milepost location is a predetermined, known location in the scan that is reached at a specific time within the scan period. The location of detected photons is preferably calculated by interpolation between the milepost locations. Photons are recorded at a rate that is dependent on the number of photons detected. Scan rate need not be limited by the number of photons expected to be counted in order to achieve a particular intensity and signal to noise ratio as is necessary in the case of pixel based sampling.

Alternatively, a signal may be indicative of the x-y position of the scan. The signal can, for example, comprise a monotonically increasing dc signal in which the amplitude of the signal corresponds to a position of the scanned beam. A detector output indicative of detection of a photon in one form triggers a sample-and-hold circuit to store the amplitude. The stored amplitude can be recorded. The amplitude can be converted to a digital value indicative of precise beam position. This technique can therefore generate a signal indicative of time of detection of a photon in order to determine photon location. Other techniques for determining the position of the scan may be used, including use of a clock or a counter activated from the beginning of the scan or other milestone.

For further precision, in certain embodiments the effect of various possibly interfering phenomena may be reduced or eliminated. These phenomena can include sampling delays that may occur in the acquisition of x-y position information and photon detection, differences between the positions indicated by the signal indicative of scanner positions and actual scanner positions. Other such phenomena may be the result of inertia of a scanning element or torque in an arm that rotates to drive a scanning component. Torque can result in different angular positions of opposite ends of a drive arm. By taking these types of phenomena into account, precision may be even further improved in certain embodiments of the present invention.

In some embodiments, photon counting may take place at high scan rates without the need to account for the number of photon counts in a sample. Image frames in raster space can be generated after the counts are registered and location data is stored. Thus, using a single data set, a dynamic event can be viewed to observe changes occurring over time by comparing images formed from sequential sample frames. Alternatively, the event can be viewed statically on different time scales.

Availability of complete sets of data in time and space can enable further forms of processing of the data, including post-hoc analysis. Post-hoc analysis of the data can allow further analysis of the sample even after the sample may become either unavailable or unresponsive to further excitation radiation.

In some embodiments, since multiple photons are acquired and statistical approaches are used to determine spatial locations of photon clusters, measurement is not limited by the diffraction limit, such as defined by the Rayleigh criterion (0.6λ/NA) inherent in optical measurements. Consequently, certain embodiments of the present invention can provide for resolution finer than that available from apparatus whose resolution is limited by the diffraction limit.

The foregoing is a brief summary of various aspects of varying embodiments of the present invention. This Summary is not exhaustive; additional features and advantages of the invention or various embodiments will become apparent as this specification proceeds. In addition, it is to be understood that embodiments of the invention need not necessarily address all issues noted in the Background nor include all features or advantages noted in this Summary or in the balance of this specification.

BRIEF DESCRIPTION OF THE DRAWINGS

The preferred and other embodiments are specified in connection with the following drawings in which:

FIG. 3 consists of FIGS. 3a and 3b, in which FIG. 3a illustrates photons that have been detected and their positions within one degree of freedom and in which FIG. 3b illustrates a sum of probability density functions of the photons in FIG. 3a;

FIG. 4 consists of FIGS. 4a and 4b, in which FIG. 4a illustrates photons that have been detected associated with an image feature and in which FIG. 4b represents a summation of the probability density functions of the positions of the photons of FIG. 4a;

DETAILED DESCRIPTION OF THE PREFERRED EMBODIMENTS

Figure 1:
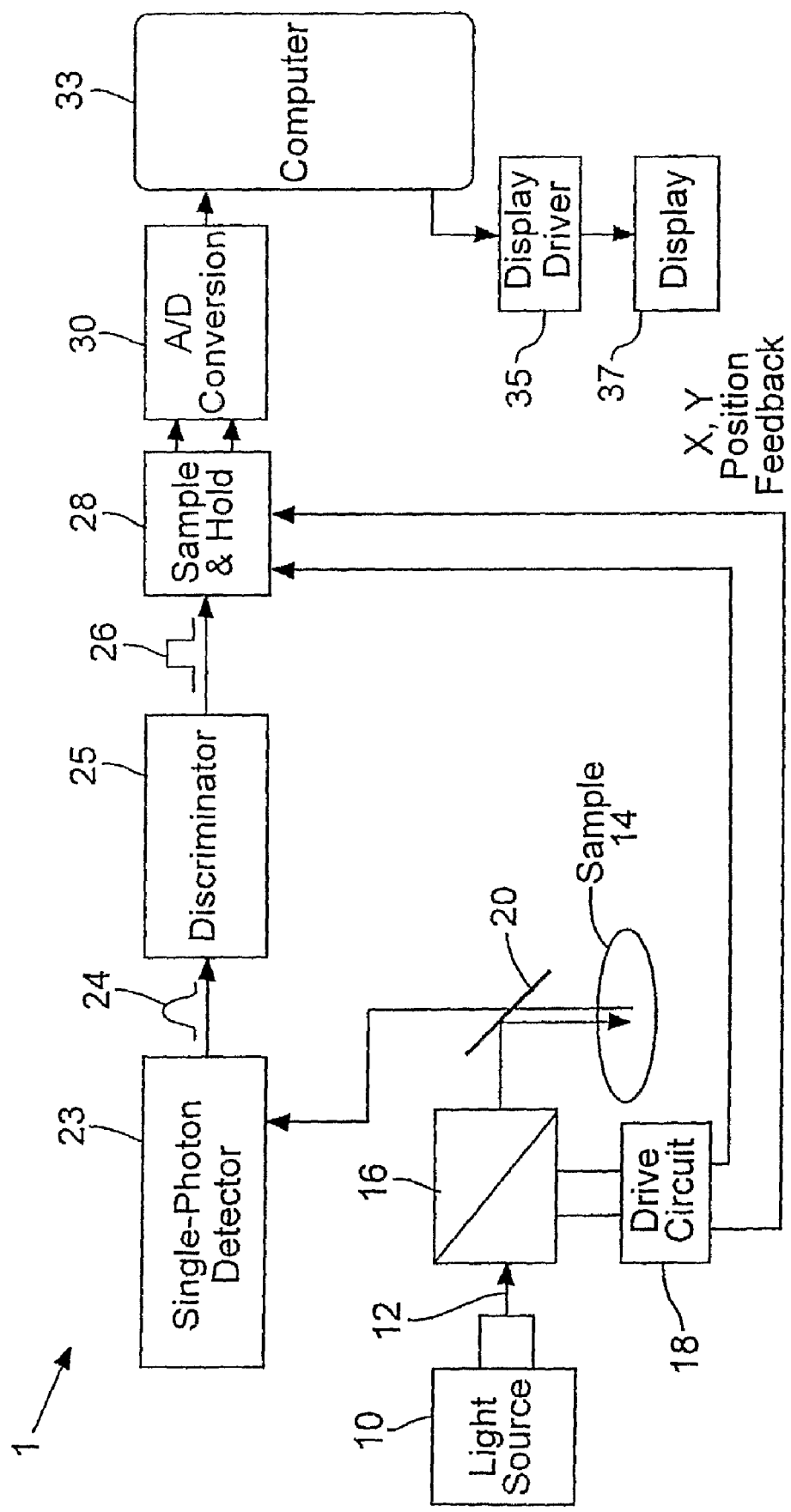
FIG. 1 is a block diagram of a system in which signals indicative of scan position are produced when a photon is detected.

With reference to FIG. 1, a system 1 constructed in accordance with an embodiment of the present invention is illustrated. A light source 10, generally a laser, provides a light beam 12 to illuminate a sample 14. Light is scanned across the sample 14 by an x-y scanner 16. The x-y scanner 16 provides a scan pattern which may be a periodic linear repetitive scan, spiral scan, or other scan pattern. Over a scan period, the scanner 16 will scan the light beam 12 over the entire sample 14 in a scan frame. The term scan frame is used to distinguish the frame from an image frame comprising pixels of a sensor which are illuminated simultaneously. In alternative embodiments, the scanner 16 is an x-y-z scanner.

The scanner 16 is driven by signals from a drive circuit 18. Many forms of scanners for directing light in a scan pattern are well known in the art. Galvanometer scanners directing rotation of a mirror to move scanned light in first and second degrees of freedom, piezo-actuated scanners and MEMS (microelectromechanical systems) tip/tilt mirror scanner are among the scanners that may be used. Since the drive circuit 18 provides an input to determine the location of the scan, the drive circuit 18 produces a signal indicative of a current position of the scanner 16. In one embodiment, the scanner 16 is a non-raster scanner as further described in our co-pending U.S. patent application Ser. No. 10/795,205, filed Mar. 4, 2004, entitled METHOD AND APPARATUS FOR IMAGING USING CONTINUOUS NON-RASTER PATTERNS, published as U.S. Patent Application No. 20040217270, on Nov. 4, 2004, the disclosure of which is incorporated by reference herein in its entirety.

In a well-known manner, a dichroic mirror 20 directs the light beam 12 from the scanner 16 to the sample 14. The dichroic mirror passes light emitted from the sample 14 to a single photon detector 23. The single photon detector 23 may comprise, for example, a photomultiplier tube or an avalanche photodiode or avalanche photodiode array. Avalanche photodiode arrays reduce well-known adverse effects due to dead time inherent in avalanche photodiode response. The distribution of each photon in space is approximated based on a point spread function of the optical system embodied in the instrumentation.

In accordance with this embodiment, the drive circuit 18 produces a signal having a value uniquely associated with one position within a scan during each scan interval. This value may be, for example, a monotonically increasing dc value as the scanner 16 progresses through the scan pattern. This value is applied to provide a potential level to the sample and hold circuit 28. When a photon is detected by the single-photon detector 23, an output pulse 24 is produced and coupled to apply an input to a discriminator 25. The discriminator 25 produces a square wave output 26 to provide a clear rising edge and falling edge coupled to a sample and hold circuit 28, which could comprise, for example, a well-known RC (resistor-capacitor) circuit. The sample and hold circuit 28 is coupled to sense the signal indicative of actual location of the scanned light in the sample being viewed. The sample and hold circuit 28 maintains a potential level which is converted to a digital signal by the analog to digital converter 30. The output of the sample and hold circuit 28 is a signal indicative of the position of the scan.

Outputs of the analog to digital converter 30 may be stored in a computer 33. As stated above, the current position of a scan also correlates with time elapsed since the beginning of the scan period. A current x-y position, or x-y-z position, of the scanner 16 has a one-to-one correspondence with the elapsed time from the beginning of a scan. Therefore, an alternative signal indicative of the position of the scan is a scan signal indicative of the elapsed time from the beginning of a scan. The time of occurrence of detection of each photon is registered by the computer 33. Consequently the position of each sensed photon is determined. As further described below, the computer 33 may be utilized to provide a time associated with each photon detection. Imprecision in the resolution and sample locations obtained during a scan due to an inability of the scanner 16 to faithfully follow the command signal can be corrected using an accurate position feedback signal from the scanner 16. The computer 33 may also include known video circuitry to produce an image in response to stored values. The values are provided to a video display driver 35 to produce an image on a display 37.

In one form, the location, or site, of the origin of every photon within the image is determined and the time at which a photon is detected may also optionally be recorded. The locations of the sources of individual photons are acquired with reference to positions of corresponding photons in a scan frame and without reference to physically defined pixels. A location from which the photon was sensed is the location at which the scanner was directed at the time the photon was sensed. While it can be desirable to sense every photon to seek to derive the maximum amount of sample information for a given amount of input illumination, images can still be generated in accordance with embodiments of the present invention if fewer than all photons are sensed or if groups of photons are sensed within a given scan period of a given scan area.

Figure 2:
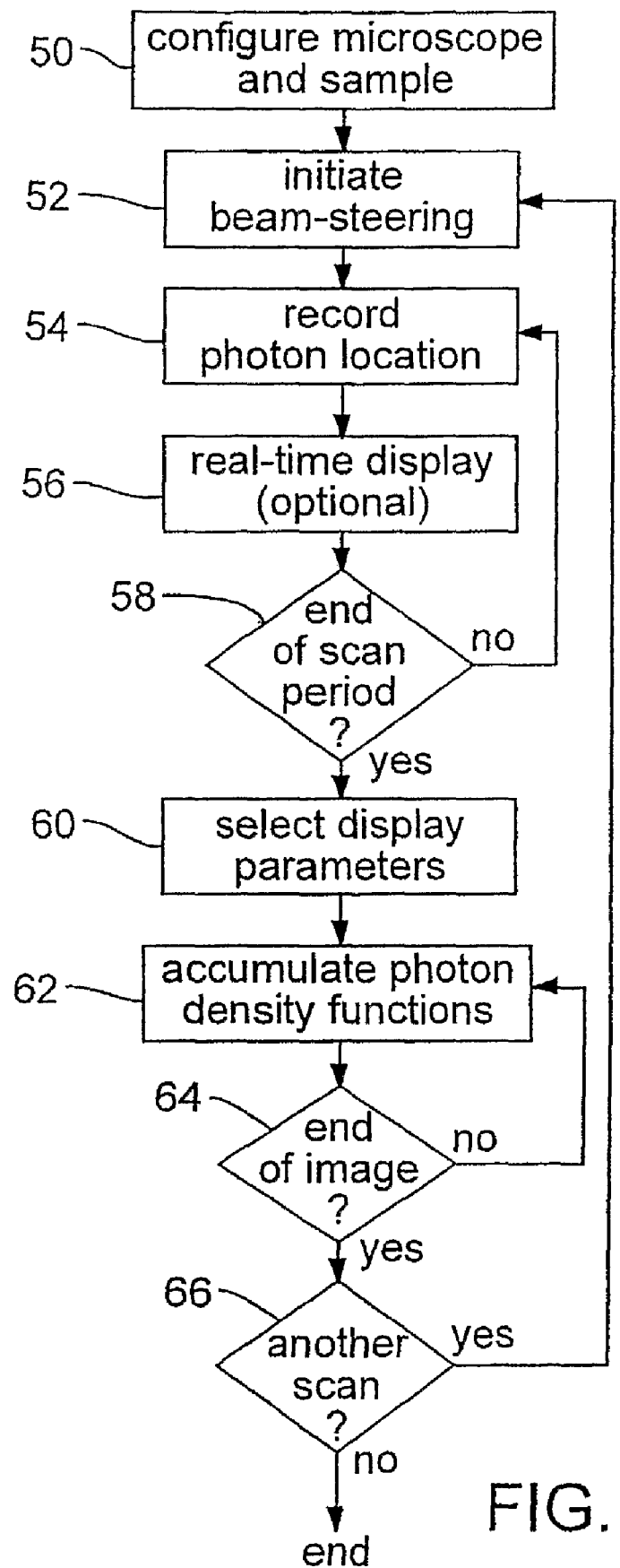
FIG. 2 is a flow diagram of the preferred method of utilizing the system shown in FIG. 1.

With reference to FIG. 2 the processes of determining photon location and producing an image comprise a first step 50, at which an operator places the sample 14 in the microscope system 1. In the next step 52, scanning of the light beam 12 over the sample 14 is initiated. Photon location is then generated 54 if and when photons are detected by the single-photon detector 23. A display of position information 56 may then be provided at the display 37. If a scan period is not complete 58, operation continues, and detected photons will again have their locations recorded 54. After a scan period, operation proceeds for further data processing 58.

Display parameters, e.g. raster locations, are selected 60 to provide a framework so that recorded photon locations in non-raster space can be mapped into raster images on the display 37. Display parameters also include a grey scale to display density functions. Mapping is required since the recorded data has a finer resolution than the pixels within the raster. In other embodiments, in which scans are also taken of successive depths of the sample 14, a set of sample data is mapped into three-dimensional voxel space. Probability density functions are accumulated 62. Probability density functions may be accumulated, for example, by a distributive or an associative method. In the associative method, an intensity value is calculated based on distances to a number n of nearest photons for each pixel. In a distributive method, each photon record is accessed and mapped into one or more raster locations. In this method, both the x and y locations can be sampled to a high degree of precision. Therefore, the probability density function of a single photon can make fractional contributions to may pixels. In one embodiment, they are sampled with 12-bit resolution. This level of resolution on one axis yields a two-dimensional image resolution of $2^{12} \times 2^{12}$, or 16 Megapixels. This level of image resolution may be described as a 16 Megapixel raster space. The accumulation of photon density functions is continued until processing of an image of a scan is completed 64. Another scan may be initiated 66 or operation may be complete 66.

Figure 3:
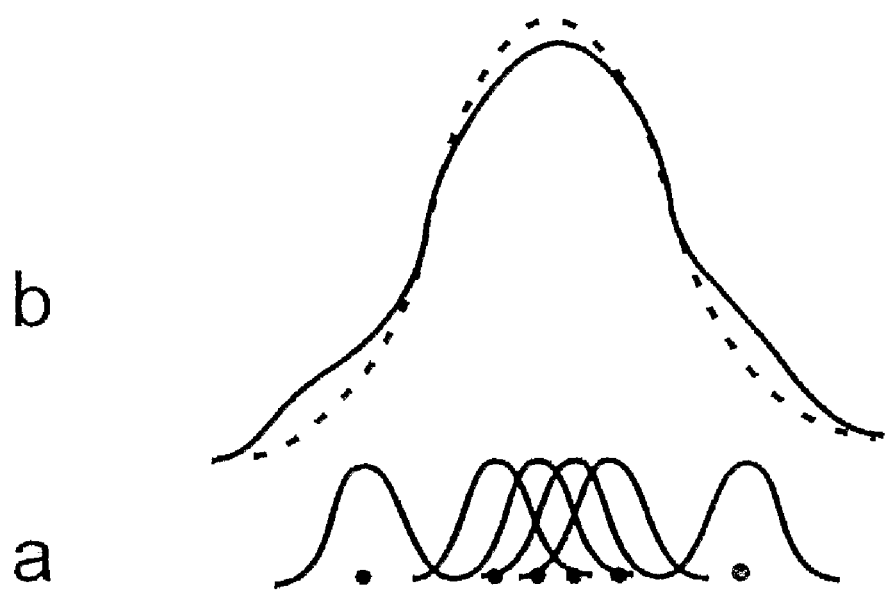
Figure 4:
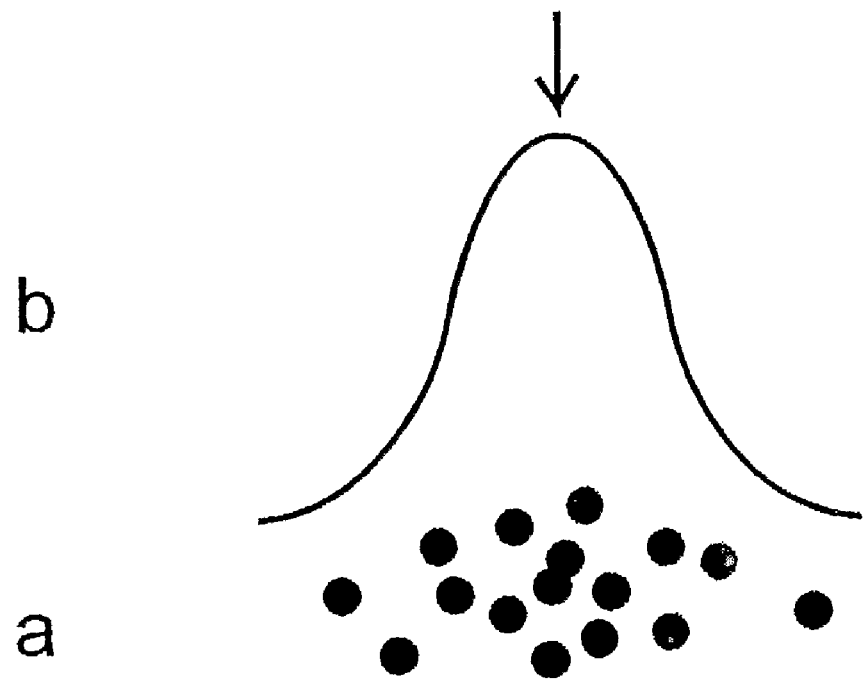

FIGS. 3 and 4 are illustrations of sensed photons and associated probability density functions. FIG. 3 consists of FIGS. 3a and 3b. In FIG. 3a, solid circles each represent a photon that has been detected and its position within one degree of freedom. Associated with each photon is a probability density function. The horizontal extent of FIG. 3 defines a region that could, for example, correspond to a pixel. Summing these probability functions yields the solid curve in FIG. 3b. Summing of photon probability density functions causes the solid curve to converge to an ideal distribution curve represented by the dashed curve. This summing of probability density functions requires fewer photons to converge to the ideal density distribution associated with an image feature than are required using conventional pixel binning. As a result, certain embodiments of the invention can provide greater sensitivity.

FIG. 4 consists of FIGS. 4a and 4b. In FIG. 4a, solid circles represent photons that have been detected that are associated with an image feature. FIG. 4b represents a summation of the probability density functions of the positions of the photons of FIG. 4a. The center of the curve in FIG. 4b, indicated by an arrow, represents the central location of the image feature as determined from the summation. The resolution of the central position obtained in this statistical manner is less than diffraction limit of light, $0.6\lambda/NA$. This physical limit is thus overcome by certain embodiments of the present invention.

Figure 5:
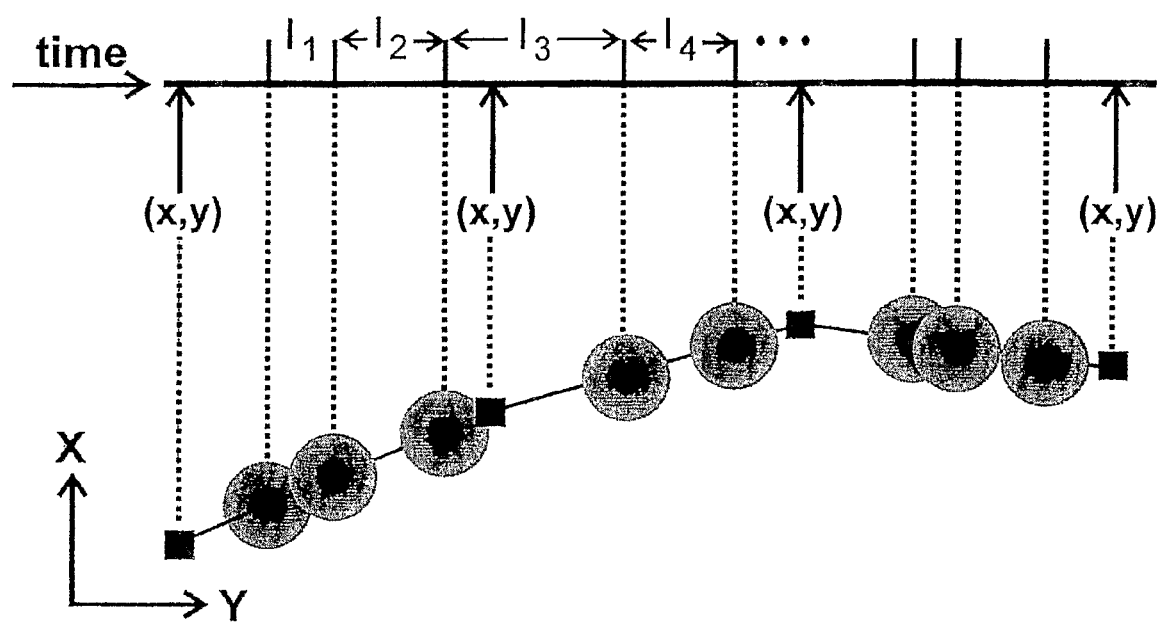
FIG. 5 is an illustration of data collected in an embodiment in which time intervals between pulses are measured in order to determine locations of corresponding photons.

FIG. 5 is an illustration of data collected in an embodiment in which time intervals between pulses are measured in order to determine locations of corresponding photons. Data may be collected using the apparatus of FIG. 1. However, rather than having a sample and hold circuit 28 store a potential level in response to each square wave 26, a pulse output indicating time of production of the square wave 26 is produced. Additionally, the circuit of FIG. 1 produces periodic "milepost" pulses having constant interpulse intervals. Each milepost pulse corresponds to a known position of a scanning beam in the scan pattern of the scanner 16.

In FIG. 5, the horizontal axis represents time. The curve plotted in x-y coordinates indicates the path of the scanning beam. In the present example, the scanning pattern comprises a spiral path. The solid dots represent locations from which a photon is received, and the circles surrounding each dot represents the point spread function inherent in the optical system of the confocal microscope system 1. The squares represent milepost beam locations. Each point in time during a scan has a unique corresponding x-y position. The position of the scan at the occurrence of each milestone pulse is known. In the present example, photon detection pulses are produced, for example, at the ends of intervals $I_0$, $I_1$, $I_2$, $I_3$ and $I_4$. The computer 33 performs linear interpolation to determine the location of each detected photon. In this example, interpolation is done between times indicated by each one of a pair of consecutive milepost beam locations which surround a particular end of an interval. However, interpolation could be done between other pairs of milepost beam locations surrounding an end of one of the intervals $I_0$, $I_1$, $I_2$, $I_3$ and $I_4$. In another alternative form, a plurality of interpolations may be performed respectively between each of a plurality of pairs of milepost beam locations. The plurality of interpolation results could be averaged or otherwise processed. Based on the point spread function, an estimate of the spatial distribution is made to generate images as described above.

Certain embodiments can thus provide for measurement of the actual locations of detected photons. Once the locations are measured, precise values indicative of the locations are stored. A complete set of location data in time and space is provided, enabling further analyses to be performed. It is not necessary to repeat an experiment in order to use different measurement parameters. Locations can be determined to a far greater degree of precision than is available in currently available displays techniques. The precision is not limited by the physical diffraction limit inherent in optical measurements because image frames are constructed by summing photon probability density functions. This requires fewer photons to converge to an ideal density distribution associated with a feature image than are required using conventional pixel binning. Resulting increased sensitivity of embodiments of the present invention permits reduction or elimination of adverse effects of over-illumination of samples.

The data obtained as described above may be processed in a number of different ways. Data thus obtained can readily be rendered in a histogram format for commonly used analyses, such as fluorescence correlation spectroscopy. Alternatively, an interval clock relative to the timing of a pulsed laser can be triggered by photon detection during data acquisition, and fluorescence lifetimes can be analyzed. In another variation, detected photons can be categorized according to their energy content and assigned an appropriate distinguishing color. In addition, it is possible to temporally expand and/or contract a data set acquired during a single high-speed acquisition period. Consequently, flexibility is provided in extracting kinetic information concerning the dynamics of the process being imaged.

Figure 7:
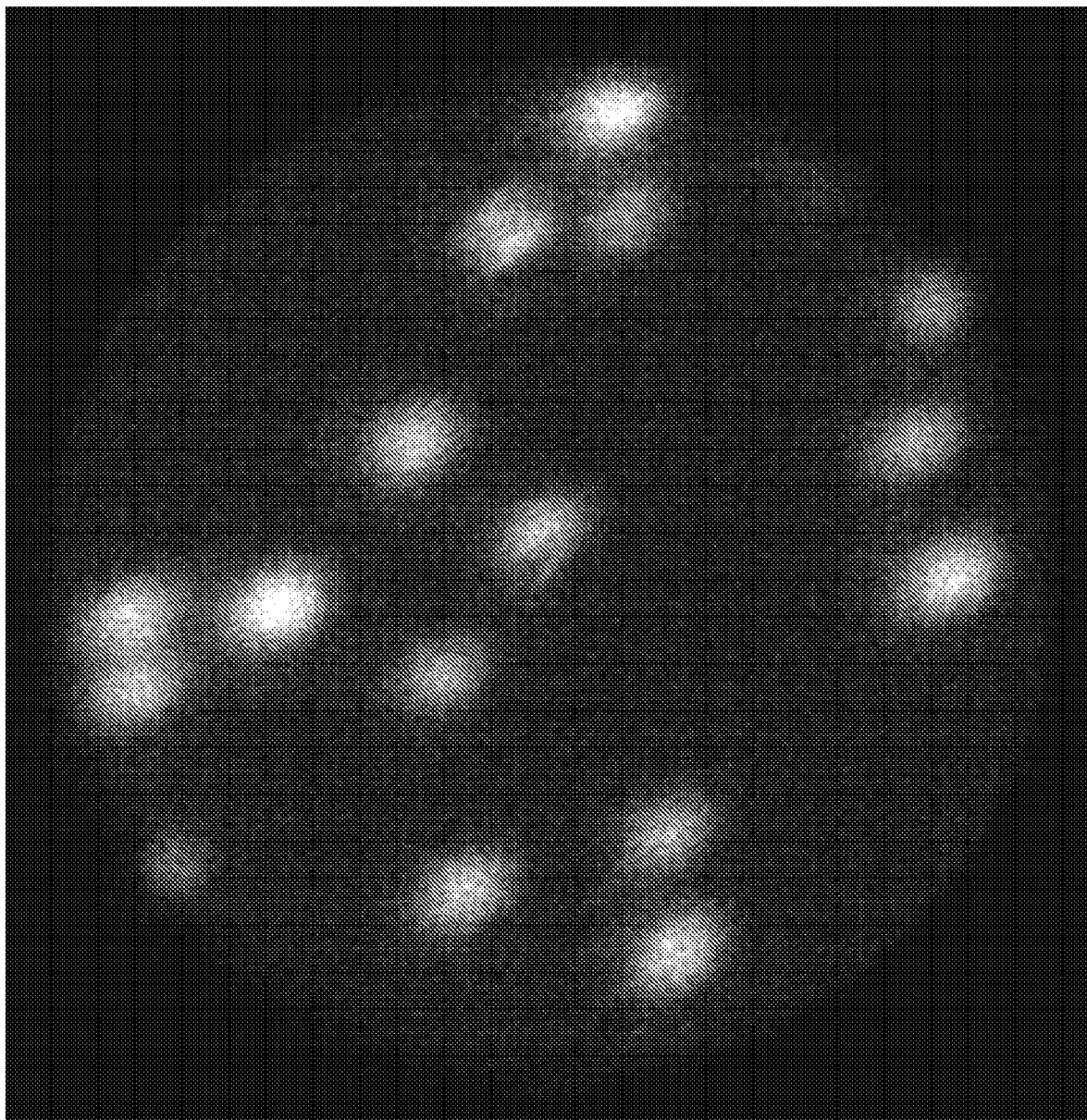
FIG. 7 is an illustration of beads detected by an embodiment of the present invention; the beads are fluorescently labeled and 100 nm in mean diameter. In the present illustration, they were imaged using a 40×, 0.95 numerical aperture (NA) microscope objective.

In some embodiments, repeated scans of a sample allow for comparison of one scan to another, and corresponding elements of one scan to another. The scans may be consecutive or non-consecutive, and the elements may be images, portions of images, or photons or sets of photons. Alternatively, positions of photons measured over integrated groups of scan periods may be compared. With appropriate compensation for noise and thermal expansion, movements in the subnanometer range may be detected. FIG. 7 is an illustration of 100 nm beads that have been detected utilizing the system 1.

Figure 6:
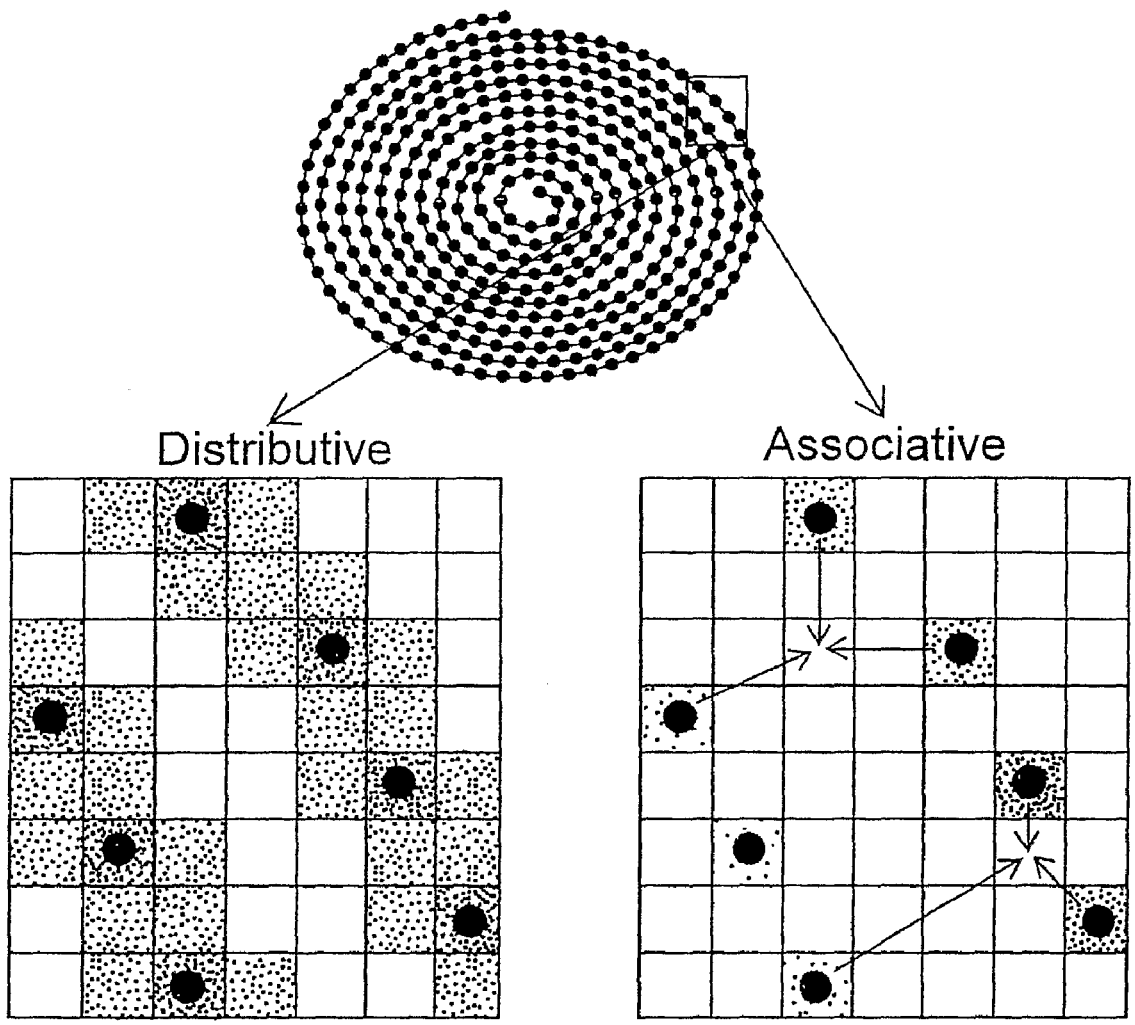
FIG. 6, consisting of FIGS. 6a, 6b and 6c, illustrates mapping of sensed positions into display raster space.

Another use of the photon detection data is to produce an image on a display. Photon position data is determined to a high degree of resolution and stored. In order to produce a display, the recorded positions of photons may be mapped into the raster space of a display. FIG. 6, consisting of FIGS. 6a, 6b and 6c, is useful in understanding embodiments of one method for mapping. In FIG. 6, FIG. 6a represents a non-raster scan (NRS) pattern, FIG. 6b is a chart illustrating a "distributive" method of mapping and FIG. 6c represents an "associative" method of mapping.

With regard to the distributive method, "n" nearest 2-dimensional raster display pixels are considered as pixels to which one photon scan location can be assigned. As in the associative method described below, the influence of each newly acquired sample on nearby raster pixels can be weighted to the distance between the location of the sample point and the location of the display pixel (e.g. inversely proportional to produce linear interpolation). In addition, the time since a pixel was last updated can be taken into account. Raster (i.e. grid) locations in the track of the spiral pattern are assigned sampled intensity values and weight factors. One suitable weight factor is inversely proportional to the distance from the actual spiral path. Other functions of distance can be used. Raster intensity values are then assigned based on the intensities/weights at each location or interpolated from neighboring pixels if no weights/intensities have been stored (a situation illustrated as white grids above). An advantage of this scheme is that most of the computation required to produce raster images can be performed one point at a time, as each sample is acquired. The distributive method requires more computational time and is better suited for producing a final raster display image, once a complete non-raster sample set has been acquired.

In the associative method, the "n" nearest sampled (i.e. non-raster) points to each 2-dimensional (raster) display pixel are found. By weighting non-raster sample points inversely proportionally to the distance between the location of the sample point and the location of the raster display pixel, it is possible to rapidly generate an accurate representation of non-raster data with smooth transitions in the raster grid display. Each raster pixel is assigned a value based on an average intensity that is weighted. A weighting factor may be inversely proportional to the distance between the raster location and the spiral sample location. Other functions of distance can be used. In this example showing how the intensity values of two pixel locations (pointed to by the collection of arrows) are computed, three nearest spiral samples are used to make the calculation. In both schemes illustrated In FIGS. 6a and 6b, relative weight factors are represented as grayscale intensity, where darker locations are weighted more heavily.

A significant advantage that can be achieved with some embodiments of both mapping methods is that the number of non-raster samples can be independent of the number of raster display pixels. Thus, if high temporal resolution (i.e. a high frame rate) is desired, a small number of samples along a non-raster pattern can produce a roughly uniform distribution of samples along a raster or non-raster pattern. If high spatial resolution is desired, then more "spirals" as well as data points along the spirals can be selected. When tracking rapid dynamic behaviors or making comparisons with spatial-temporal mathematical models, the non-raster pattern can be used to select just enough spatial resolution while maximizing temporal resolution. The number of sample points per image and frame rate can be chosen under software control to be any values on a continuous scale (i.e. single points can be added or subtracted). Maximum values are governed only by sinusoidal scanning frequency and photon detection efficiencies, not by the characteristics of display devices.

As an example of using a non-raster pattern with an NRS-LSCM, if each sample required a dwell time of 0.5 microseconds to gather a sufficient number of photons and 2000 samples were needed for adequate spatial resolution, then a frame rate of 1000 frames/second could be achieved. Greater frame acquisition rates can be chosen completely under software control (i.e. with no modifications to hardware). In these examples, a low number of spiral samples (450 points along the spiral scan) in combination with a low spiral sample to raster pixel ratio have intentionally been used to simplify illustration of the different mapping methods.

If desired, the highest possible scan rates can be used without considering the number of photons being acquired. Once a complete data set has been acquired, raster space images having desired intensity values can be constructed by combining one or more scan frames. Thus, using a single data set, a dynamic event can either be viewed to observe changes occurring over time by comparing images formed from sequential sample frames, or the event can be viewed statically on different time scales by combining data from more than one sample frame. In the latter case, the accuracy of parameters obtained for a dynamic event described at high temporal resolution by one or a few scan frames can be compared with those derived from images of the same event obtained over a longer interval. Useful information can thus be provided as to the interval of scanning needed to obtain a given level of accuracy.

Storing of the data thus obtained allows for further use of the data. Frame images can be reconstructed and viewed at different temporal rates, thereby permitting compression or expansion of viewing of an overall data set. The availability of complete data sets in space and time makes it possible to conduct repeated post-hoc analyses rather than repeating an experiment using different measurement parameters. This saves cost and reduces inconvenience. Availability of post-hoc analysis guarantees that analysis may be made even when a sample is no longer available or is no longer responsive to radiation excitation. This feature provides a number of advantages including the ability to (i) compare conventional images using pixel "bins" with those accumulated using probability density functions, and (ii) determine the exact sequence of photonic responses relative to other events.

Another use of photon event sampling is to overcome prior art limitations of scanning microscopes in achieving required special resolution and detail in the imaging of a biological sample or inspection of properties of the surface of a material. Doing so with prior art scanning microscope techniques usually involves the frequent need to utilize high numerical aperture (NA) microscope objectives that require immersion in a fluid medium and close apposition to the sample or surface to achieve the required spatial resolution and detail. To minimize sample manipulation and increase throughput, however, it is advantageous to utilize lower NA objectives having longer working distances and with an air interface between the objective and the sample or surface.

Embodiments of photon event distribution sampling (PEDS) also can be used to counteract the loss of spatial resolution and detail associated with use of objectives having lower NA values and longer working distances and permits such objectives to be used for the above noted examples. For example, the 100 nm mean diameter fluorescent beads shown in FIG. 7 were imaged with a 40× objective having a NA value of 0.95 using a wavelength of 488 nm. According to the Rayleigh criterion the minimal resolvable object for this objective using this excitation wavelength would have a diameter of 300 nm. Thus, using PEDS, spatial resolutions typically achievable in the past only under specialized conditions using high NA oil-immersion objectives, are achieved with objectives having both an air interface and a significantly greater working distance.

EXAMPLE

Application

One application of an embodiment of the present invention is measurement of release of calcium ion, $Ca^{2+}$, from intracellular sarcoplasmic reticulum (SR) stores in cardiac cells. $Ca^{2+}$ release activates the contractions of the heart in order to pump blood throughout the body. $Ca^{2+}$ is released through ryanodine receptor (RyR) $Ca^{2+}$ channels present in SR membranes and information concerning the functional properties of these channels, as they exist inside of heart cells, can help in understanding how contraction of the heart is activated and regulated. Since RyR channels are present in intracellular membranes, they cannot be studied using conventional microelectrode-based electrophysiological techniques. However, changes in intracellular $Ca^{2+}$ can be measured non-invasively by monitoring fluorescence from dyes, such as fluo-3 introduced into the cytoplasm of the cell, which increases when $Ca^{2+}$ binds to the dye.

Small increases in fluo-3 fluorescence observed in cardiac cells, termed $Ca^{2+}$ sparks, are thought to be due to release of $Ca^{2+}$ from a small number of RyR channels. $Ca^{2+}$ sparks have been proposed to represent elemental events that are first steps in activating contraction in the heart. As such they have the potential to provide information concerning the activity and properties of RyR channels in intact cardiac cells. A situation that complicates relating the properties of $Ca^{2+}$ sparks directly to those of RyR channels is that spark properties can be influenced by conditions and factors within heart cells not related to the activity of RyR channels. These factors interact with one another and cannot be easily manipulated individually in intact cells and thus, it has proven difficult to assess in a direct manner experimentally how each factor and condition alters $Ca^{2+}$ spark properties. To date, workers in the field have attempted to use computer modeling and simulations to dissect influences by cellular factors and conditions from those related to the activity of RyR channels.

An alternative and complementary approach to this problem, is an in vitro, optical bilayer system, which permits imaging of fluo-3 fluorescence in response to $Ca^{2+}$ flux through single RyR channels reconstituted into artificial planar lipid bilayer membranes simultaneously with electrical recording of single RyR channel $Ca^{2+}$ currents.

Hardware

A suitable confocal microscope included in the system 1 of FIG. 1 comprises a BioRad MRC 600 laser scanning confocal microscope system (LSCM) from BioRad Laboratories in Hercules, Calif. In a typical embodiment, the laser 10 may comprise an ion or solid-state laser emitting in ultraviolet to infrared wavelengths, such as those available from Melles Griot of Rochester, N.Y. and Blue Sky Research of Milpitas, Calif. The scanner 16 may comprise an x-y steering device, including mirrors mounted on closed loop galvanometers, such as those available from Cambridge Technology, Inc. of Cambridge, Mass. One embodiment utilizes a pair of Cambridge Technology Model 6800 CLG, which are rated as being capable of scan frequencies of 500-600 Hz over mechanical scan angles of $\leq 10°$. These frequencies were determined for raster scanning (i.e. repeatedly starting and stopping). Scan frequencies of slightly greater than 1 kHz (limited by safeguard circuitry on the driver card) can be obtained using non-raster scanning and position feedback signals to establish sample position in non-raster space.

The dichroic mirror 20 is available from Semrock, Inc. of Rochester, N.Y. The laser beam is focused onto a specimen or sample by a device, such as a microscope objective.

Movement of the beam-steering device and scanning of the radiation is dictated by command signals originating from a computer under software control and converted to appropriate analog voltages by a digital-to-analog converter with resolution dictated by the spatial resolution requirements of the measurement being made, commonly available from commercial sources, such as National Instruments. The beam steering device can be moved in either a raster pattern or in non-raster patterns to scan the electromagnetic radiation across the specimen or sample. Photons, due to reflected or fluorescent light, originating from a focal plane in the specimen or sample pass through the wavelength-selective device and are counted as single events by a single event detector, such as an avalanche photodiode available from Perkin Elmer Optoelectronics of Wellesley, Mass. or a photomultiplier tube available from Hamamatsu Corporation of Bridgewater, N.J. operating in a single photon counting mode. A single pulse is sent from the detector to a discriminator circuit for every photon detected.

The BioRad 600 LSCM can scan a single line in the x dimension in ~2 msec. Therefore a full frame x, y image containing 768×512 pixels or 512 x, t-line scans (with each line containing 768 pixels) can be obtained in ~1 sec. The rise time of a $Ca^{2+}$ spark in a cardiac cell is ~8-12 msec. Consequently, using this system it is possible to obtain only 6 points or less to describe the onset of this event. Single x, t-line scans are employed to achieve the highest scan rates possible. In this approach, spatial sampling is collapsed to a single dimension, as the same line is scanned repeatedly as rapidly as possible. Since $Ca^{2+}$ sparks are 4-dimensional events occurring in x, y and z spatial dimensions, as well as in time, this approach also results in suboptimal spatial sampling and potential problems in data interpretation.

One reason for the limited temporal resolution of the MRC 600 in some LSCM systems is that mirrors mounted on separate closed-loop galvanometers (CLG) are used to scan a laser beam in the x and y dimensions in a raster pattern. This requires that the laser beam be turned around at the beginning and end of each line, which involves stopping and starting a CLG. Since the shaft of a CLG has significant mass and relatively large mirrors are typically used to accommodate laser beams whose diameters have been expanded for optical reasons, considerable inertia is involved. The time required to reverse the direction of the laser beam is a significant portion of the time required to scan a single line, which imposes a fundamental limit on the scan rates that can be achieved. In addition, since pixel size in current LSCM systems is determined by the pixel clock interval, uniform sampling during a scan requires that the laser beam move at a constant velocity. Thus, the time required for the CLG to accelerate to a constant velocity can also impact scanning capabilities.

System Optimization and Desirable Attributes

The discriminator circuit is adjusted to separate pulses caused by photons from those caused by random noise and each pulse generated by a photon results in a digital pulse being sent to a sample & hold circuit. Each time a digital pulse is received a corresponding set of voltages representing the x and y positions of the beam steering device at the time the photon was detected are retained by the sample & hold circuit. The beam steering device position signals are converted to digital signals and passed to the computer by an analog-to-digital converter with resolution appropriate for the measurement being made, commonly available from commercial sources, such as National Instruments of Austin, Tex. The position of each photon detected within the image domain is transmitted via a display driver to a display device, such as a computer monitor, to form an image of the illuminated region of the specimen or sample. The display can utilize either a raster or non-raster scanning format.

The intensity value assigned to each photon in the spatial domain of the image can be adjusted as a probability density function formulated relative to the point-spread-function of the illuminating radiation and the probability of exciting emission from a fluorophore positioned within the illumination point spread function. The focal plane in the specimen or sample being illuminated by the electromagnetic radiation is selected under computer control via focus control circuitry controlling the position in the z-axis at which the radiation is focused in the specimen or sample. This control is currently typically implemented via a serial (USB) port interface with the focus control circuitry. As is the case with x and y position signals, voltage-indicated z positions may also be passed to the sample & hold circuit 28 and subsequently to the computer 33 via an analog-to-digital converter channel. It should be noted that algorithms commonly used to eliminate photons originating from above and below the focal plane and enhance images obtained with the approach presently described.

The NRS-LSCM thus described offers particular advantages for imaging dynamic processes. Such dynamic processes include change in intracellular $Ca^{2+}$ ($Ca^{2+}$ sparks and waves) involved in tissue activation and intracellular signaling, changes in membrane potential in excitable tissues (e.g. heart and brain), or the spread of activation within the GI tract. Images of these events, as well as of many other cellular processes, share in common the fact that they contain relatively low spatial frequencies. Therefore, relatively low sampling frequencies (and consequently high scan rates) can be used to establish their properties in an adequate manner.

Embodiments of the present invention are designed to be capable of imaging events involving intermediate-to-low spatial frequencies at maximal possible (photon-limited) sampling rates. Moreover, because spatial resolution capabilities have not been sacrificed to obtain greater temporal resolution, the NRS-LSCM system will equal the data collection rate performance of systems for imaging samples containing high spatial frequencies, where greater sampling rates (and lower scan speeds) are used.

In the embodiments described above, the scan format is a type of non-raster scan identified as a spiral scan. Other scan formats may be utilized, including other raster and non-raster scan formats.

It is to be understood that the foregoing is a description of preferred and other embodiments. The foregoing description therefore is not to be construed as itself limiting of the scope of the invention.

What is claimed is:

1. A data generating method comprising:
    A) scanning a sample during a scan period over a scan pattern comprising a plurality of positions;
    B) detecting a packet of electromagnetic energy received from the sample in response to the scanning during the scan, resulting in an initial image file whose size is equal to the number of photons detected; and
    C) associating the packet of electromagnetic energy with a first position in the scan pattern.

2. The data generating method of claim 1 wherein the detecting step (B) further comprises detecting a plurality of subsets of packets of electromagnetic energy received from the sample in response to the scanning during said scan period of time; and wherein the associating step (C) further comprises associating each subset of packets among the plurality of subsets of packets of electromagnetic energy with a corresponding position in the scan pattern.

3. The data generating method of claim 2 wherein each subset of packets consists of one packet of electromagnetic energy and the detecting step (B) further comprises producing an output indicative of detection of the packet of electromagnetic energy.

4. A data generating method according to claim 3, further comprising combining data produced over successive scan periods in accordance with a function.

5. A data generating method according to claim 4, comprising mapping the data into at least one image.

6. A data generating method according to claim 5, comprising associating each scan position with a subdivision of the image.

7. A data generating method according to claim 6, further comprising establishing subdivisions of the image each corresponding to a pixel of a display.

8. A data generating method according to claim 7 further comprising producing a pixel signal in correspondence with data assigned to each of a plurality of respective pixels and providing said pixel signals to a display driver.

9. A data generating method according to claim 6, wherein the scan is three-dimensional.

10. A data generating method according to claim 9, further comprising subdividing each image into voxels.

11. A data generating method according to claim 5, further comprising providing a fluorescent sample and scanning said sample with excitation radiation.

12. A data generating method according to claim 11, wherein detecting comprises viewing photons from the sample with a confocal microscope and focusing said photons on a photon detector.

13. A data generating method according to claim 11, wherein detecting comprises viewing photons from the sample with a confocal microscope and focusing said photons on a photon detector.

14. A data generating method according to claim 5, further comprising providing a reflecting sample and scanning said sample with excitation radiation.

15. A data generating method according to claim 4, further comprising generating a position function for detected packets of electromagnetic energy.

16. A data generating method according to claim 15 wherein generating a position function comprises generating a probability density function.

17. A data generating method according to claim 16, further comprising summing probability densities, determining spatial distribution, and resolving image features.

18. A data generating method according to claim 17, further comprising summing spatial distribution over a predetermined time period.

19. The data generating method of claim 16, further comprising forming an image feature from the probability density functions.

20. The data generating method of claim 16, further comprising forming an image by displaying the probability density functions of each detected photon and summing the distributions where overlap occurs.

21. A computer programmed to perform the steps of claim 1.

22. A computer according to claim 21, wherein the detecting step (B) further comprises detecting a plurality of subsets of packets of electromagnetic energy received from the sample in response to the scanning during said scan period of time; and wherein the associating step (C) further comprises associating each subset of packets among the plurality of subsets of packets of electromagnetic energy with a corresponding position during the scan period.

23. A computer according to claim 22, wherein each subset of packets consists of one packet of electromagnetic energy and the detecting step (B) further comprises producing an output indicative of detection of the packet of electromagnetic energy.

24. A computer according to claim 23, further programmed to map the data into an image.

25. A computer according to claim 24, further programmed to establish subdivisions of the image each corresponding to a pixel of a display.

26. A computer according to claim 25, wherein the scan is three-dimensional and further programmed to subdivide each image into voxels.

27. A computer according to claim 26, further programmed to sum probability densities, determining spatial distribution, and resolving image features.

28. A computer according to claim 22, further programmed to combine data produced over successive scan periods in accordance with a function.

29. A computer according to claim 28, further programmed to associate each scan position with a subdivision of the image.

30. A computer according to claim 29, further programmed to produce a pixel signal in correspondence with data assigned to each of a plurality of respective pixels and providing said pixel signals to a display driver.

31. A computer according to claim 29, further programmed to respond to sensing of the individual packets of electromagnetic energy with a photon detector.

32. A computer according to claim 31, further programmed to generate a position function for detected packets of electromagnetic energy.

33. A computer according to claim 32, further programmed to produce an image frame by summing spatial distribution over a user-selected time period.

34. A computer according to claim 31 wherein generating a position function comprises generating a probability density function.

35. The data generating method of claim 1 wherein associating the packet of electromagnetic energy with a first position in the scan pattern is carried out in a pixel-less manner.

36. The data generating method of claim 1, wherein associating the packet of electromagnetic energy with a first position in the scan pattern associates the packet with a discrete spatial position.

37. A data generating method comprising:
scanning a sample during a scan period over a scan pattern comprising a plurality of positions;
detecting a plurality of subsets of packets of electromagnetic energy received from the sample in response to the scanning during the scan and producing an output indicative of detection of the packet of electromagnetic energy;
associating each subset of packets among the plurality of subsets of packets of electromagnetic energy with a corresponding position in the scan pattern;
combining data produced over successive scan periods in accordance with a function;
generating a position function for detected packets of electromagnetic energy comprising generating a probability density function; and
forming an image by displaying the probability density functions of each detected photon and summing the distributions where overlap occurs.

38. A computer programmed to perform the steps of claim 37.

39. A data generating method comprising:
scanning a sample during a scan period over a scan pattern comprising a plurality of positions;
detecting a plurality of subsets of packets of electromagnetic energy received from the sample in response to the scanning during the scan and producing an output indicative of detection of the packet of electromagnetic energy;
associating each subset of packets among the plurality of subsets of packets of electromagnetic energy with a corresponding position in the scan pattern;
combining data produced over successive scan periods in accordance with a function;
generating a position function for detected packets of electromagnetic energy comprising generating a probability density function; and
forming an image feature from the probability density functions.

40. A computer programmed to perform the steps of claim 39.

* * * * *